US 6,673,599 B2

(12) United States Patent
Rietschel et al.

(10) Patent No.: US 6,673,599 B2
(45) Date of Patent: Jan. 6, 2004

(54) PROCESS AND APPARATUS FOR DEFOAMING A BIOREACTOR

(75) Inventors: Wolfgang Rietschel, Söhrewald (DE); Wolfgang Kahlert, Körle (DE); Reinhard Kiel, deceased, late of Melsungen (DE), by Sabine Kiel, executor

(73) Assignee: Sartorius AG (DE)

( * ) Notice: Subject to any disclaimer, the term of this patent is extended or adjusted under 35 U.S.C. 154(b) by 0 days.

(21) Appl. No.: 10/251,554

(22) Filed: Sep. 19, 2002

(65) Prior Publication Data

US 2003/0068813 A1 Apr. 10, 2003

(30) Foreign Application Priority Data

Oct. 5, 2001 (DE) .......................................... 101 49 132

(51) Int. Cl.[7] ................................................ C12M 1/21
(52) U.S. Cl. ...................... 435/301.1; 435/812; 96/176; 96/177; 96/178; 95/261; 210/194
(58) Field of Search ............................ 435/301.1, 812; 96/176, 177, 178; 95/261; 210/194

(56) References Cited

U.S. PATENT DOCUMENTS

| 3,917,526 | A | * | 11/1975 | Jennings ...................... 210/641 |
| 4,340,677 | A | * | 7/1982 | Hitzman ...................... 435/246 |
| 5,143,525 | A | * | 9/1992 | Sotirianos ...................... 95/242 |
| 5,800,704 | A | * | 9/1998 | Hansen ...................... 210/169 |
| 6,303,028 | B1 | * | 10/2001 | Marks et al. ............... 210/169 |
| 6,465,243 | B2 | * | 10/2002 | Okada et al. ............. 435/301.1 |
| 6,514,411 | B2 | * | 2/2003 | Pressley et al. ............. 210/608 |
| 6,561,078 | B1 | * | 5/2003 | Hughes ........................ 99/277 |

FOREIGN PATENT DOCUMENTS

| DE | 41 42 967 A1 | 12/1991 |
| DE | 299 07 596 U 1 | 7/1999 |
| EP | 0 031 590 A1 | 8/1981 |

* cited by examiner

Primary Examiner—David A. Redding
(74) Attorney, Agent, or Firm—Chernoff, Vilhauer, McClung & Stenzel, LLP

(57) ABSTRACT

There is disclosed a defoaming rotor capable of skimming foam from the surface of the fermentation broth in a bioreactor, separating the solid and liquid components from the gaseous component of the foam, and returning the solid and liquid components to the broth.

9 Claims, 1 Drawing Sheet

PROCESS AND APPARATUS FOR DEFOAMING A BIOREACTOR

BACKGROUND OF THE INVENTION

In the case of chemical and biochemical reactions of substances in an aqueous solution, gas bubbles frequently form, which accumulate and rise to the surface of the solution. As this occurs, liquid and solid components of the solution are entrained therewith, which leads to the buildup of foam on the surface of the liquid. In the case of fermentation and/or digestion processes in bioreactors wherein broth is subjected to the action of microbes such as bacteria and yeast fungi, the accumulation of foam on the surface of the broth is particularly heavy. This foam accumulation in bioreactors occurs principally due to the evolution of carbon dioxide. Such a buildup of foam leads not only to the entrainment of liquid and solid components, thereby causing loss of a portion of the fermentation broth, but also effectively isolates the broth from atmospheric oxygen and blinds aeration filters, thereby interfering with or even stopping the fermentation process. To overcome these problems various schemes have been developed to prevent the formation of undesirable foam in a bioreactor or to repress, disperse or remove the foam.

For some time it has been known to mix in with the fermentation broth chemical antifoam agents to repress or diminish the formation of foam. Such antifoam agents, however, contaminate the fermenting broth, and must be removed later. Such agents can also negatively affect the reaction processes in the bioreactor and impair the exchange of biosubstances. In addition, due to the presence of fillers, thickeners, and coagulation agents in the antifoam agents, the agents tend to blind microfilters used in processing the broth, especially where membrane filters are employed.

To prevent such plugging of microfilters by antifoam agents, a process is disclosed in EP 0 391 590 A1, which uses an oil-based material encapsulated in a water-soluble granule antifoam agent. Although such an antifoam agent does reduce blinding of microfilters, it nevertheless still contaminates the fermentation broth.

DE 41 42 967 discloses another way of removing foam in bioreactors, by disseminating a liquid antifoam agent directly onto and/or into the foam itself. Although this method is effective at reducing foam buildup, it also still contaminates the broth.

Because of the foregoing drawbacks of antifoam agents, a number of attempts have been made to develop defoaming methods and apparatus which permit foam accumulation and then simply skim the foam off the broth, mechanically separate the foam's solid and liquid components from its gaseous components and convey them into a collection container or back into the bioreactor to recombine with the original fermentation broth.

One such apparatus is described in DE 299 07 596 U1. The head space of the bioreactor is provided with a foam overflow line, which permits discharge of the foam into a collection container external to the bioreactor. The head space of this collection container is provided with a gas outlet open to the atmosphere. Foam that builds up within the head space of the bioreactor is gradually forced out and into the collection container. In the collection container the gaseous components separate from the liquid and solid components of the foam, and escape through the gas outlet. The liquid and the solid components of the foam concentrate in the bottom of the collection container and can be removed through an outlet line in the bottom of the collection container by a screw type pump. Because the foam virtually fills the entire head space of the bioreactor above the fermenting broth, the fermentation process is starved of oxygen and so slows, which must be compensated for by complicated, artificial aeration. Moreover, because of the unrestricted foam generation and escape of the foam from the bioreactor, an undesirable separation of a significant portion of the fermenting broth occurs, which brings about a substantial loss of liquid and cells which have been entrained in the foam.

It is therefore the goal of the present invention to provide a process and apparatus for the defoaming of the fermentation broth in a bioreactor which is effective, economical and space-saving, wherein the foam is promptly removed from the surface of the broth and the liquid and solid components of the foam are separated from the gaseous components and returned to the fermentation broth and wherein no contamination of the broth occurs.

BRIEF SUMMARY OF THE INVENTION

The aforementioned goal is achieved by the provision of a foam guiding means, at least one skimmer plate rotating about an axis, and at least one centrifuge chamber, arranged together in the form of a rotor. The rotor is placed inside a bioreactor and above the broth surface, so that, by continuous rotation of the rotor, foam is mechanically skimmed off the broth surface and conducted into the centrifuge chamber, wherein the solid and liquid components of the foam are separated from gaseous components by centrifugal force and returned to the fermentation broth.

At lest two significant advantages are achieved by the inventive process and apparatus: (1) the addition of a chemical antifoam agent with its several known drawbacks becomes unnecessary; and (2) breakdown of the fermentation broth is avoided. The chemical reactions in the fermentation broth can proceed without interruption and any subsequent filtering of the broth is possible without the otherwise customary blinding of a microfilter. Since the rotor is positioned above the liquid level of the broth, and it rotates within the foam but not within the fermenting broth, a modest amount of energy is required to drive the rotor and thus, an economical defoaming operation is provided.

DETAILED DESCRIPTION OF PREFERRED EMBODIMENTS

Figure 1:
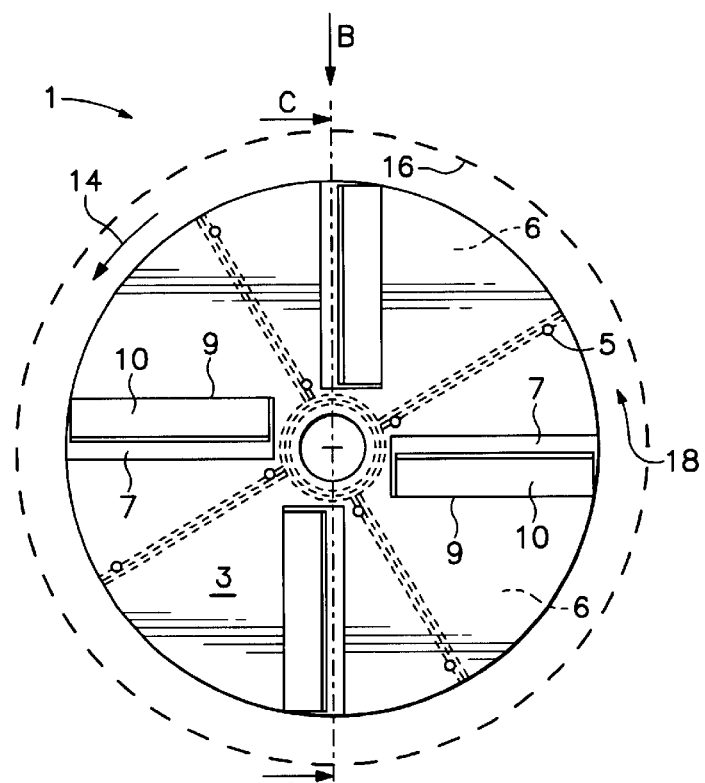
FIG. 1 is a schematic drawing of an exemplary defoaming rotor of the present invention, as viewed from below.
Figure 2:
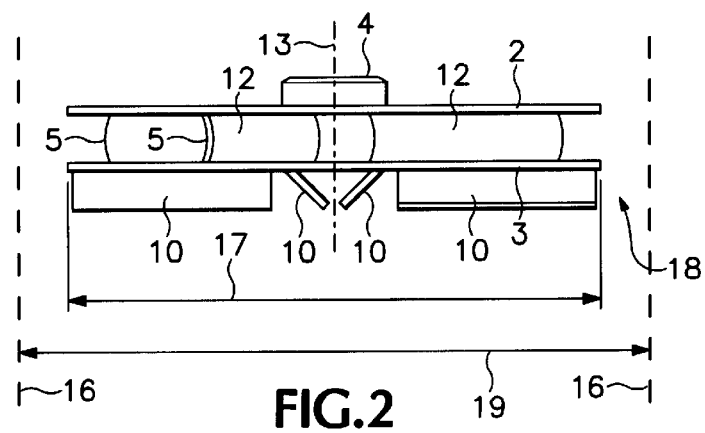
FIG. 2 is a side view of the rotor of FIG. 1 taken from vantage point B.
Figure 3:
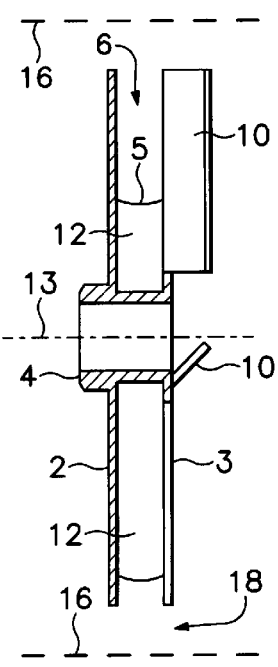
FIG. 3 is a sectional view of the rotor of FIG. 1 taken through the plane C—C.

Referring to the drawings, wherein the same numerals refer to like elements, there is shown in FIGS. 1–3 a bioreactor defoaming apparatus comprising a defoaming rotor 1 adapted for insertion into a bioreactor in close proximity to the surface of a fermentation broth. Rotor 1 comprises an upper disk 2 and a lower disk 3, which are vertically displaced relative to each other and secured to a common hub 4. Between disks 2 and 3 are four radial deflection vanes 5, placed at an equal radial distance from each other, and which divide the space between the two disks into four centrifuge chambers 6 of substantially equal size. Each centrifuge chamber 6, i.e., each of the individual sectors above circular disk 3, is provided with a radial slot 7, which is located slightly outside of the center between adjacent deflection vanes 5. Skimmer plate 10 is attached to the trailing edge 9 of radial slot 7 and angled downward. Deflection vanes 5 are longitudinally concave on that side facing the trailing edge 9 of radial slot 7 so as to form runoff troughs 12.

Defoaming of the fermentation broth in a bioreactor is accomplished by placing rotor 1 in the bioreactor proximate to the surface of the fermentation broth and rotating the same in the radial direction 14 about its vertical axis 13. Foam which has accumulated above the surface of the fermentation broth is captured and carried off by skimmer plate 10 and forced through radial slot 7 into a corresponding centrifuge chamber 6. In centrifuge chamber 6, the foam encounters deflection vane 5, which compresses it and sets it into rotary motion, whereby due to the centrifugal force created, the heavier liquid and solid components of the foam are separated from the lighter gaseous components. The heavier components then are forced radially outwardly by deflection vanes 5 to be ejected against the inner surface 16 (shown in phantom) of the bioreactor wall and flow down the wall by gravity back into the fermentation broth.

Because of its low profile the inventive defoaming rotor can be readily integrated into a bioreactor and be made vertically adjustable so that skimmer plates 10 can rotate at a minimum safety clearance above the surface of the fermentation broth. Since the rotor rotates only in the air and/or within the foam, it encounters little resistance, and so only a small driving force of the associated drive motor (not shown) is necessary. The drive motor is preferably an electric motor located outside of the bioreactor, e.g., upon a cover for the bioreactor, and is connected to rotor hub 4 by a drive shaft (not shown). In order to assure an unimpeded flow of the solid and liquid components of the foam down the inner surface 16 of the bioreactor wall and back into the fermentation broth, the outside diameter 17 of lower disk 3 is significantly smaller than the inside diameter 19 of the inner surface 16 of the bioreactor wall. This difference in diameters effectively creates an annular space 18 between the periphery of lower disk 3 and the inner surface 16 of the bioreactor wall.

For optimal efficiency, prior to its operation the defoaming apparatus is oriented vertically to the surface of the fermenting broth by means of a vertical adjustment (not shown) such that the skimmer plate is slightly above the surface of the broth, that is, it neither dips into the fermenting broth nor is too high in the foam.

By its contact with a deflection vane, the foam in the centrifugal chamber is set into rotation, whereby the foam is compressed, thereby causing an initial separation of the gaseous components of the foam from its liquid and solid components. Complete separation of the components of the foam is effected by the rotational centrifugal force, which leads to a radially inward separation of the lighter gaseous components from the heavier liquid and solid components, which move radially outward. The liquid and solid components ultimately are ejected radially outwardly along the deflection vane against the inner wall surface of the bioreactor, whereupon they flow downward by gravity, returning to the fermenting broth.

The inventive defoaming rotor is constructed relatively simply and cheaply and preferably has a low profile. Its design is such that it can be retrofit to any model bioreactor at any time. The drive motor, which is preferably an electric motor, could be placed within the bioreactor above the rotor. However, for sterility, especially in the case of food product production, the motor is best placed outside the bioreactor, e.g., on the bioreactor's cover. The motor, in this case, would be connected with the rotor by a drive shaft axially penetrating the bioreactor cover.

So that an optimal collection and discharge of the solid and liquid components of the foam can be achieved the deflection vane is shaped so as to present a side that is concave facing the direction of rotation. In this manner, the deflection vane forms a radial trough curved on its horizontal or longitudinal axis.

Each skimmer plate is a downwardly inclined plate fastened to the rear radial edge of the corresponding radial slot and angled in the direction of rotation, wherein the angle of inclination is preferably approximately 45°. A skimmer plate designed in this manner provides, as it operates in conjunction with the radial slot, an effective foam removal with a high throughput. Further, the skimmer plate may be simply and economically fabricated by simply bending down that part of the lower disk which was cut out to form the radial slot.

For greater throughput and to avoid an imbalance of the rotor, a plurality of centrifuge chambers are preferably equally radially disposed about the rotor's axis, each with a corresponding skimmer plate, radial slot and deflection vane. Four such centrifugal chambers per rotor are preferred. The defoaming rotor is advantageously provided with an adjustment device for its vertical positioning above the surface of the broth with a small clearance between the skimmer plate and the broth's surface before the defoaming rotor is placed in operation.

If the bioreactor in question is provided with a stirring device that rotationally stirs the fermentation broth, then the defoaming rotor, for improved efficiency, should be designed to run in a direction opposite to the direction of rotation of the broth caused by the stirring device.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. Apparatus for defoaming a bioreactor comprising a rotor (1) rotatable about a vertical axis, said rotor being provided with at least one skimmer plate (10) for the removal of foam, at least one centrifuge chamber (6) for the separation of solid and liquid components of the foam, said at least one centrifuge chamber having a radial slot (7) and at least one radial deflection vane (5) for the radial ejection of the solid and liquid components of the foam.

2. The apparatus of claim 1 wherein said rotor (1) includes at least two vertically separated disks (2, 3) secured to a common hub (4) wherein said radial slot (7) and said skimmer plate (10) are located on the lower of said two disks.

3. The apparatus of claim 2 wherein said at least one radial deflection vane (5) is located between said two disks.

4. The apparatus of claim 3 wherein said at least one radial deflection vane (5) is concave facing the direction of rotation of said rotor.

5. The apparatus of claim 1 wherein said skimmer plate (10) is inclined at a downward angle in the direction of rotor rotation.

6. The apparatus of claim 5 wherein said downward angle is approximately 45°.

7. The apparatus of claim 1 including four centrifuge chambers (6) of approximately equal size.

8. The apparatus of claim 1 wherein said rotor (1) is vertically adjustable.

9. A process for defoaming a bioreactor containing fermentation broth comprising inserting the apparatus of any of claims 1–8 into said bioreactor in close proximity to the surface of said broth and rotating said apparatus.

* * * * *

UNITED STATES PATENT AND TRADEMARK OFFICE
CERTIFICATE OF CORRECTION

PATENT NO. : 6,673,599 B2
DATED : January 6, 2004
INVENTOR(S) : Reitschel et al.

It is certified that error appears in the above-identified patent and that said Letters Patent is hereby corrected as shown below:

Column 2,
Line 33, change "lest" to read -- least --.

Signed and Sealed this

Twenty-third Day of November, 2004

JON W. DUDAS
*Director of the United States Patent and Trademark Office*